United States Patent
Rothaemel et al.

(10) Patent No.: US 8,785,708 B2
(45) Date of Patent: Jul. 22, 2014

(54) PROCESS FOR PREPARING $C_2$- TO $C_4$-OLEFINS FROM A FEED STREAM COMPRISING OXYGENATES AND STEAM

(75) Inventors: Martin Rothaemel, Frankfurt (DE); Walter Boll, Frankfurt (DE); Gerhard Birke, Frankfurt (DE); Harald Koempel, Neu-Isenburg (DE); Waldemar Liebner, Oberusel (DE); Hermann Bach, Heiligenroth (DE)

(73) Assignee: Lurgi AG, Frankfurt (DE)

( * ) Notice: Subject to any disclaimer, the term of this patent is extended or adjusted under 35 U.S.C. 154(b) by 1574 days.

(21) Appl. No.: 11/909,629

(22) PCT Filed: Feb. 28, 2006

(86) PCT No.: PCT/EP2006/001817
§ 371 (c)(1),
(2), (4) Date: May 28, 2010

(87) PCT Pub. No.: WO2006/105831
PCT Pub. Date: Oct. 12, 2006

(65) Prior Publication Data
US 2010/0234655 A1    Sep. 16, 2010

(30) Foreign Application Priority Data

Apr. 6, 2005  (DE) .......................... 10 2005 015 923

(51) Int. Cl.
*C07C 1/00*    (2006.01)
(52) U.S. Cl.
USPC ........................................................ 585/639
(58) Field of Classification Search
USPC ........................................................ 585/639
See application file for complete search history.

(56) References Cited

U.S. PATENT DOCUMENTS

| | | | | |
|---|---|---|---|---|
| 4,550,217 A | * | 10/1985 | Graziani et al. | 585/324 |
| 7,022,888 B2 | * | 4/2006 | Choudhary et al. | 585/639 |
| 7,405,337 B2 | * | 7/2008 | Kalnes et al. | 585/640 |
| 2006/0063956 A1 | * | 3/2006 | Kalnes et al. | 585/639 |
| 2006/0106270 A1 | * | 5/2006 | Glover et al. | 585/639 |
| 2006/0161035 A1 | * | 7/2006 | Kalnes et al. | 585/639 |

FOREIGN PATENT DOCUMENTS

| | | | | |
|---|---|---|---|---|
| DE | 3524890 | * | 1/1986 | C07C 1/24 |
| DE | 102 33 975 | * | 2/2004 | C07C 1/20 |
| WO | 97/36845 | * | 10/1997 | C07C 1/00 |

* cited by examiner

*Primary Examiner* — Patricia L Hailey
(74) *Attorney, Agent, or Firm* — Norris McLaughlin & Marcus PA

(57) ABSTRACT

In a process for the preparation of $C_2$- to $C_4$-olefins, a feed stream comprising oxygenates and steam is passed through at least one fixed-bed zone comprising zeolite catalyst, where the oxygenates are converted catalytically into olefins with high selectivity for lower olefins, and the reaction mixture leaving the fixed-bed zone is separated into a first product stream comprising $C_2$- to $C_3$-olefins and inert gas components, at least one second product stream comprising $C_{4+}$-olefins, and a third product stream consisting of aqueous phase. In order to improve the yield of lower olefins, the aim is to regulate the temperature of the catalytic reaction in accordance with a target temperature value in the range from 440 to 520° C. specified for the reaction mixture exiting the fixed-bed zone by means of a supplementary stream consisting of olefins and inert gas components fed into the feed stream.

19 Claims, 3 Drawing Sheets

PROCESS FOR PREPARING $C_2$- TO $C_4$- OLEFINS FROM A FEED STREAM COMPRISING OXYGENATES AND STEAM

This application is a 371 application of PCT/EP2006/001817 filed Feb. 28, 2006, which claims priority to the German application DE 10 2005 015 923.0 filed Apr. 8, 2005.

The invention relates to a process for the preparation of $C_2$- to $C_4$-olefins, preferably propylene, from a feed stream comprising vaporous oxygenates, preferably methanol and/or dimethyl ether, and steam and having a temperature of from 280 to 480° C., which is passed through at least one fixed-bed zone arranged in a reactor and formed from a bed of granular, shape-selective zeolite catalyst of the pentasil type, and the oxygenates are converted catalytically into olefins with high selectivity for lower olefins at a reaction temperature of from 350 to 550° C., preferably from 420 to 490° C., and the reaction mixture exiting the reactor is separated into a first product stream comprising $C_2$- to $C_3$-olefins, preferably propylene, at least one further, second product stream comprising $C_{4+}$-olefins, and a third product stream consisting of aqueous phase.

DE-A-19723363 discloses a process for the preparation of $C_2$- and $C_3$-olefins by reaction of a reaction mixture comprising methanol and/or dimethyl ether vapor and steam in an indirectly cooled tubular reactor on a shape-selective fixed-bed catalyst at temperatures of from 280 to 570° C. and pressures of from 0.1 to 1 bar. A product stream comprising $C_2$- to $C_4$-olefins and $C_{5+}$-olefins is withdrawn from the reactor, cooled, and separated into a product comprising $C_2$- and $C_3$-olefins and a product comprising $C_{5+}$-olefins.

According to DE-A-10027159, a further development of this process consists in that methanol is firstly converted into a vapor mixture comprising dimethyl ether on a fixed-bed catalyst comprising granular $Al_2O_3$ in a reactor tank. For the production of a product comprising $C_3$-olefins, a first sub-stream of the vapor mixture is fed, together with steam, into a first reaction tank filled with a fixed bed comprising shape-selective zeolite catalyst, and the intermediate discharged therefrom is fed, together with a second sub-stream of the above-mentioned vapor mixture, to a second reaction tank filled with a fixed bed comprising shape-selective zeolite catalyst. The product withdrawn from the second reaction tank is separated into a product stream comprising about 97% by vol. of $C_3$-olefins and a product stream comprising residual substances, such as $C_2$-olefins and $C_{4+}$-olefins, where the residual substance product stream is recycled into at least one reaction tank filled with zeolite catalyst.

In a process described in DE-A-19648795 far the preparation of $C_3$- and $C_4$-olefins, a feed stream comprising $C_4$- to $C_7$-olefins is converted into a product comprising $C_3$- and $C_4$-olefins, preferably adiabatically, on a shape-selective zeolite catalyst of the pentasil type accommodated in a reaction tank. This product is subsequently cooled, so that water and benzine condense out. The condensate formed is separated into a water-containing phase, an organic liquid phase and a gaseous phase comprising $C_2$- to $C_4$ olefins and small proportions of paraffins, the gaseous phase is passed through a separation device in order to separate off $C_2$- and $C_3$-olefins, and the organic liquid phase is separated by distillation into a phase comprising $C_3$- and $C_4$-olefins and small amounts of saturated hydrocarbons and a phase comprising benzine. Besides propylene, principally ethylene, n-butene-1 and isobutylene can be separated off from the phase comprising $C_3$- and $C_4$-olefins and small amounts of saturated hydrocarbons by distillation or adsorption.

U.S. Pat. No. 6,441,261 relates to a process for the conversion of a feed stream comprising an oxygenate and an inert diluent into an olefin product by passing the feed stream through a silicon-aluminophosphate catalyst arranged in a reactor tank, before which the pressure of the feed stream is from 12 to 42 at and the partial pressure of the oxygenate is from 1 to 5 at.

The object of the present invention is to improve the process described at the outset in such a way that the highest possible yield of $C_2$- to $C_4$-olefins, but very particularly of propylene, is achieved by catalytic reaction of oxygenates with reduced complexity.

This object is achieved in that a reaction pressure of from 1.0 to 3.0 bara prevails at the entry of the feed stream into the fixed-bed zone and a reaction pressure of from 0.5 to 2.0 bara prevails at the exit of the reaction mixture from the fixed-bed zone, and the temperature of the catalytic reaction is regulated in accordance with a target temperature value in the range from 440 to 520° C., preferably from 480 to 495° C., specified for the reaction mixture exiting the fixed-bed zone by means of a supplementary stream comprising olefins and inert gas components fed into the feed stream. By means of this regulation, the temperature of the feed stream at the entry into the fixed-bed zone is continuously recorded and compared with the target temperature value for the reaction mixture exiting the fixed-bed zone, and the temperature of the feed stream is thus influenced with respect to the temperature of the catalytic reaction by the supplementary stream fed into the feed stream.

Owing to the high heat capacity of the olefins and inert gas components in the supplementary stream and possible endothermic reactions due to the catalytic cleavage of higher hydrocarbons, for example $C_6H_{12} \rightarrow 2C_3H_6$, the adiabatic temperature increase in the fixed bed drops, so that the temperature at the entry of the feed stream into the fixed bed can be raised for a specified target temperature value for the reaction mixture discharged from the fixed bed. Both the selectivity for $C_2$- to $C_4$-olefins from the reaction of the oxygenates and also, owing to the temperature dependence of the degree of conversion, the oxygenate conversion itself are increased here. Overall, an increase in the yield of $C_2$- to $C_4$-olefins is thus achieved.

In order to increase the yield of $C_2$- to $C_4$-olefins, it is furthermore advantageous if the $C_{4+}$-olefins in the second product stream together with the inert gas components in the first product stream are recycled into the feed stream as supplementary stream.

The inert gas components are one or more of the substances steam, nitrogen, helium, neon, argon, hydrogen, carbon monoxide, carbon dioxide and $C_1$- to $C_4$-paraffins, by means of which the partial pressure of the reaction components is reduced and thus the selectivity and yield of $C_2$- to $C_4$-olefins, in particular propylene, are increased.

The yield of $C_2$- to $C_4$-olefins can be optimized if use is made of supplementary streams which comprise one or more of the components $C_2$- to $C_8$-olefins, preferably $C_2$-olefins and $C_4$- to $C_6$-olefins, $C_1$- to $C_8$-paraffins, preferably $C_1$- to $C_6$-paraffins, $C_5$- to $C_8$-naphthenes, preferably $C_5$- to $C_6$-naphthenes, and $C_6$- to $C_7$-aromatic compounds.

The by-product streams arising during operation of thermal and catalytic crackers or similar processes can also be used as supplementary streams.

Process-internal recycling streams can likewise be employed as supplementary streams.

The throughput of the oxygenates present in the feed stream is from 0.1 to 10 kg, preferably from 0.3 to 1.5 kg, per hour and per kg of catalyst employed.

A preferred embodiment of the process according to the invention consists in that the feed stream is fed to a reactor having a plurality of, preferably two to six, fixed-bed zones by splitting the feed stream into a number of feed sub-streams corresponding to the number of fixed-bed zones and feeding each feed sub-stream to a corresponding fixed-bed zone, where the reaction mixture discharged from a fixed-bed zone is fed to the subsequent fixed-bed zone, and the reaction mixture discharged from the final fixed-bed zone in the downstream direction is fed to a separation unit. A supplementary stream comprising olefins and inert gas components is split into a number of supplementary sub-streams corresponding to the number of feed sub-streams, and each supplementary sub-stream is fed into a corresponding feed sub-stream or into the reaction mixture exiting a fixed-bed zone and fed to the subsequent fixed-bed zone.

The invention is explained in greater detail by working examples and with reference to the attached drawings, in which.

Figure 1:
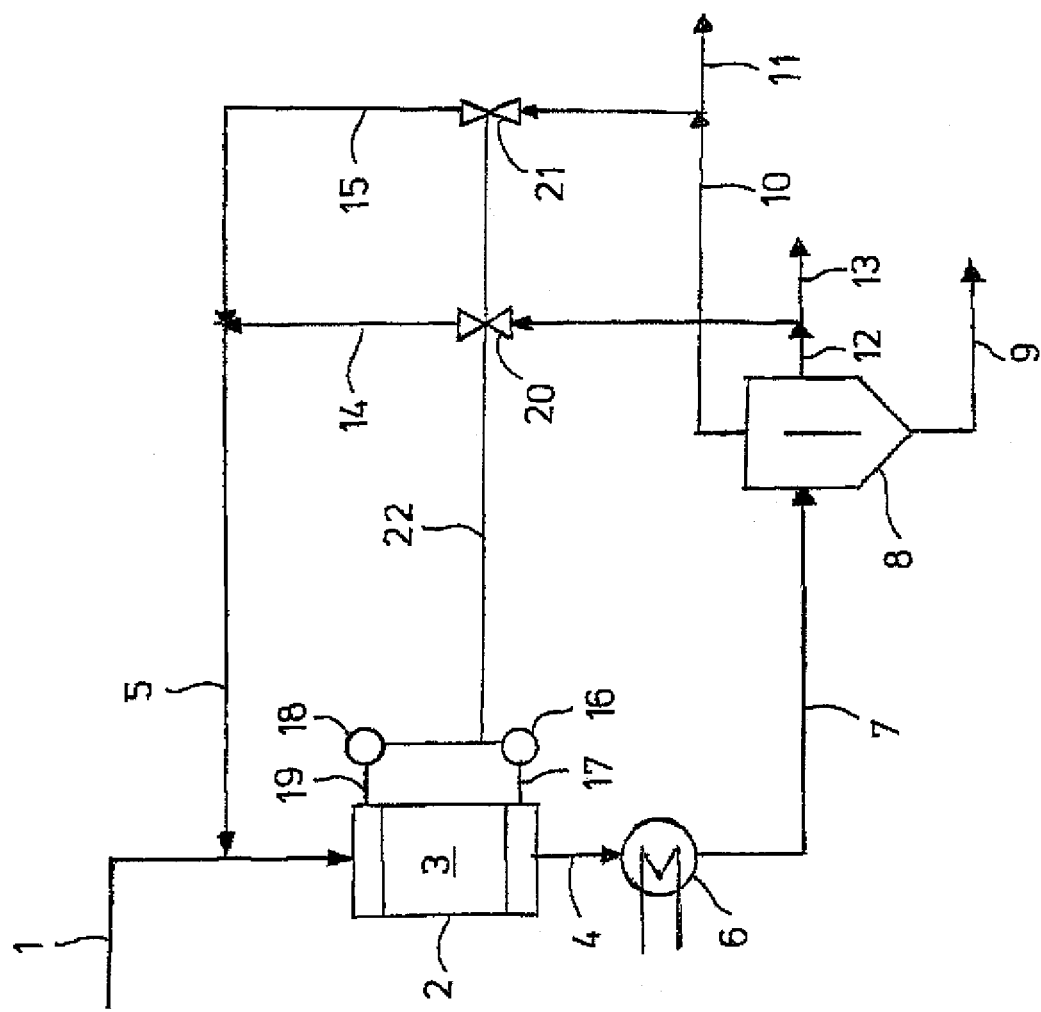
FIG. 1 shows a process flow chart with a reactor and the control scheme
Figure 2:
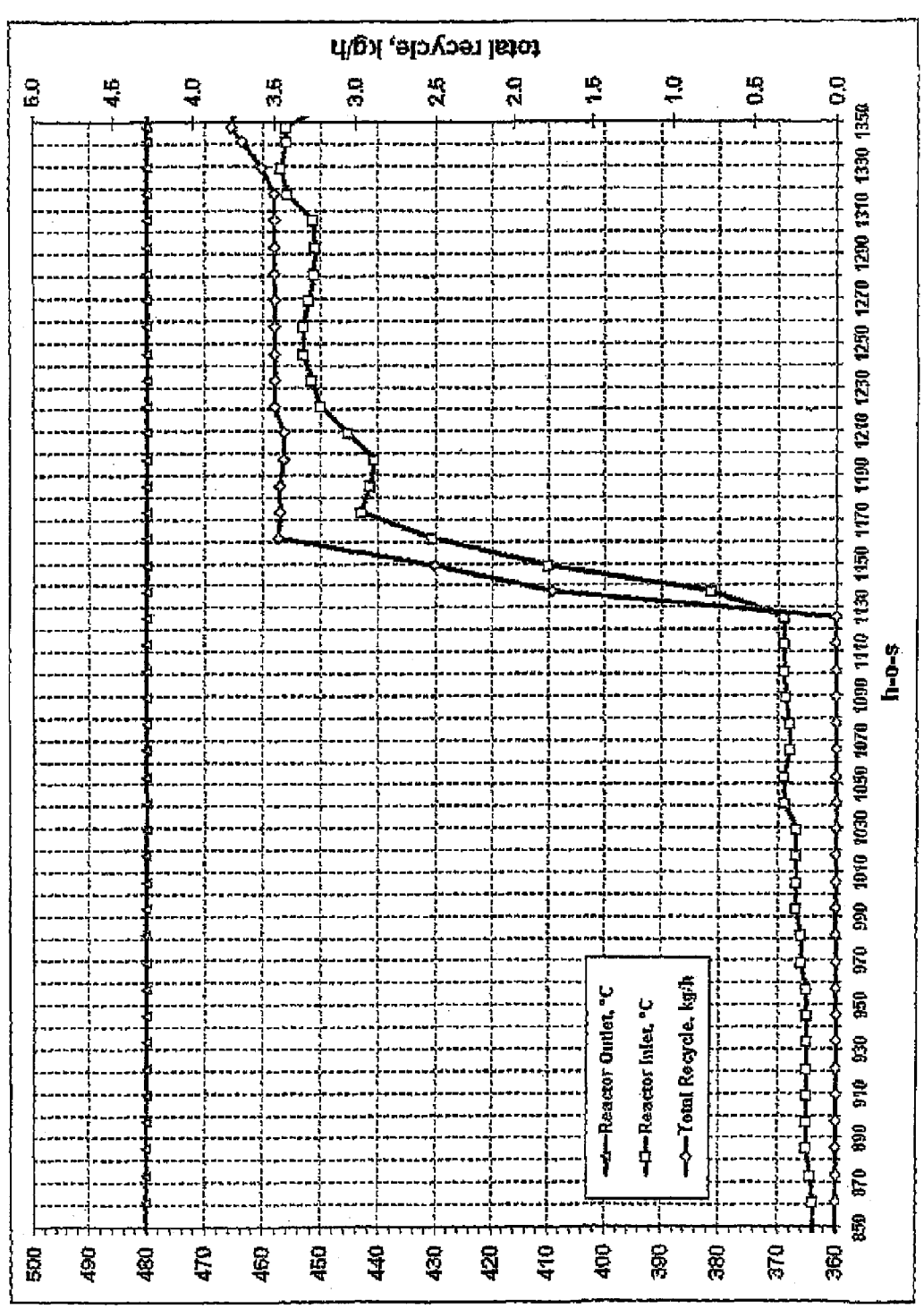
FIG. 2 shows the operation of the process with temperature profiles measured in a reactor

As shown in FIG. 1 and FIG. 2, a vapor-form feed stream comprising oxygenates and steam and having a temperature of 364-369° C. is fed via line (1) to the reactor (2) (FIG. 2, h-o-s, reactor inlet, ° C., to an operating time of 1125 h-o-s [hours-on-stream]). A bed of granular zeolite catalyst of the pentasil type having shape-selective properties and having a particle size of from 1 to 8 mm forming a fixed-bed zone (3) is arranged in the reactor (2). On passing the feed stream through the fixed-bed zone (3), an adiabatic reaction takes place, so that the temperature of the reaction mixture leaving the reactor (2) via line (4) remains constant at 480° C. (FIG. 2, h-o-s, reactor outlet, ° C., to an operating time of 1125 h-o-s). After a supplementary stream comprising olefins and inert gas components which is formed internally in the process has been recycled into the feed stream via line (5) in an amount of 3.5 kg/h (FIG. 2, total recycle kg/h), the temperature of the reaction mixture leaving the reactor can be adjusted to the target value of 480° C. by raising the entry temperature to from 420 to 430° C. The reaction mixture exiting the reactor (2) via line (4) is cooled in a condenser (6) to a temperature in the range from 25 to 80° C., so that water and hydrocarbons, in particular benzine, condense out. The condensate is fed via line (7) to a separator (8), in which separation into a gaseous first product stream comprising $C_2$- to $C_3$-olefins, a second product stream comprising $C_{4+}$-olefins, and a third product stream comprising aqueous oxygenates takes place. The third product stream comprising the aqueous oxygenates is discharged from the process via line (9). Propylene is separated off by distillation from the first product stream withdrawn from the separator (8) via line (10) and discharged from the process as principal product via line (11). The second product stream discharged via line (12) is separated by distillation into $C_6$-olefins and $C_{7+}$-olefins, with the $C_{7+}$-olefins being discharged from the process via line (13), the $C_6$-olefins being fed into line (5) via line (14), and the residual stream formed from $C_2$-olefins and inert gaseous components being fed into line (5) via line (15). The substance streams combined in line (5) form the supplementary stream, which is added to the feed stream comprising oxygenates, which is fed to the reactor (2) via line (1).

The target value of the temperature of 480° C. for the reaction mixture exiting the reactor (2) is measured by means of a temperature sensor (17) installed beneath the catalyst fixed bed (3) and connected to a measurement transducer (16), and the temperature of the feed stream entering the reactor (2) and flowing through the catalyst fixed bed (3) is measured by means of a temperature sensor (19) arranged above the catalyst fixed bed (3) and connected to a measurement transducer (18). The measured value of the entry temperature of the feed stream is compared with the specified target value of the exit temperature of the reaction mixture; if the entry temperature of the feed stream is too low, the flow regulators (20, 21) arranged in lines (14, 15) and actuated electrically via line (22) are opened, and the olefin-containing supplementary stream influencing the temperature of the feed stream is added to the feed stream. After the requisite amount of supplementary stream has been fed in, the flow regulators (20, 21) are closed again.

Figure 3:
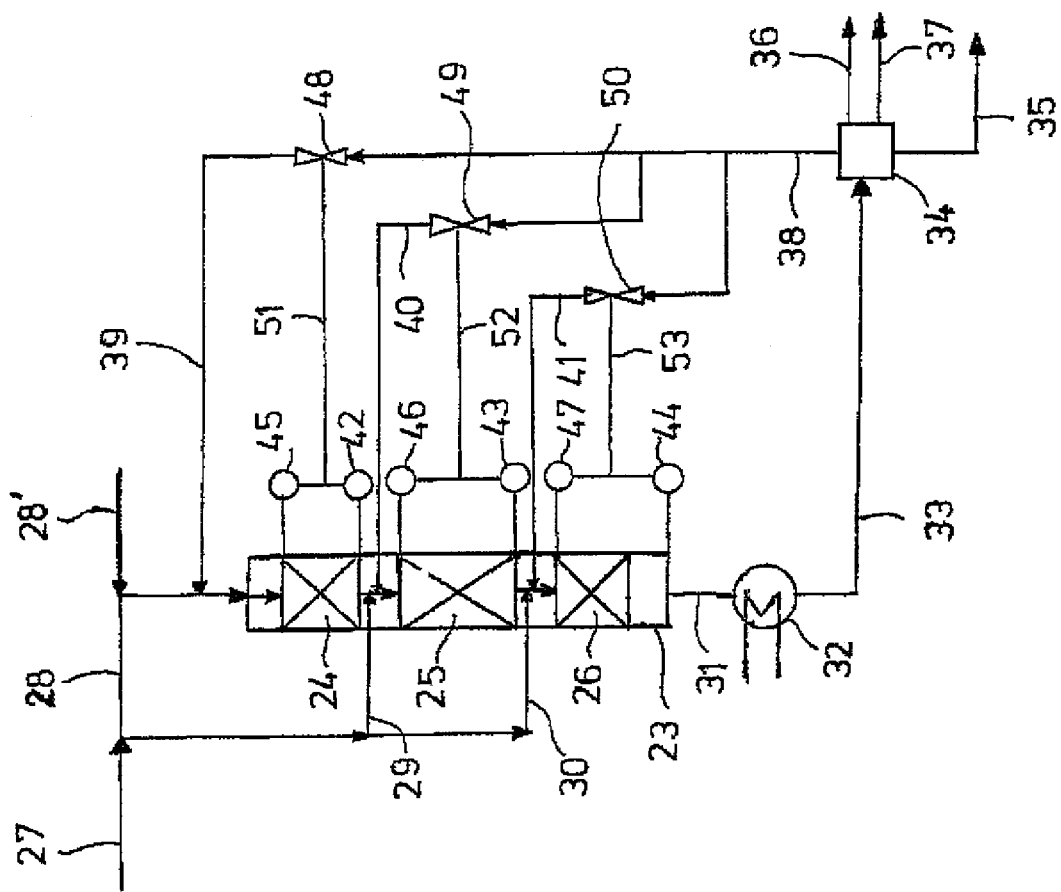
FIG. 3 shows a process flow chart with three fixed-bed zones arranged in a reactor and the control scheme.

In the process flow chart depicted in FIG. 3, three fixed-bed zones (24, 25, 26) arranged one above the other, each consisting of a bed of granular zeolite catalyst of the pentasil type having shape-selective properties and having a particle size of from 1 to 8 mm, are located in a reactor. The feed stream comprising vapor-form oxygenates and steam arriving via line (27) is mixed with a gas stream fed in via line (28') and formed from inert components and then heated to a temperature of 364° C. The feed stream mixed in this way is subsequently split into three feed sub-streams, of which one feed sub-stream is fed via line (28) to the upper fixed-bed zone (24), a second feed sub-stream is fed via line (29) to the central fixed-bed zone (25), and a third feed sub-stream is fed via line (30) to the lower fixed-bed zone (26). The reaction mixture exiting the upper fixed-bed zone (24) is fed to the central fixed-bed zone (25), and the reaction mixture exiting the central fixed-bed zone (25) is fed to the lower fixed-bed zone (26). The reaction mixture discharged from the lower fixed-bed zone (26) via line (31) is cooled to a temperature of from 25 to 80° C. in a condenser (32), so that water and hydrocarbons, in particular benzine, condense. The condensate passes via line (33) into a separation unit (34), in which it is separated into a gaseous, first product stream comprising $C_2$- and $C_3$-olefins, a second product stream comprising $C_{4+}$-olefins, and a third product stream comprising aqueous oxygenates. The third, oxygenate-containing product stream is discharged from the process via line (35), propylene as principal product is separated off from the first product stream by distillation and then discharged from the process via line (36), the second product stream is split into $C_6$-olefins and $C_{7+}$-olefins by distillation, and the $C_{7+}$-olefins are discharged from the process via line (37). The $C_6$-olefins and the $C_2$-olefins formed on distillation of the first product stream leave the separation unit (34) together via line (38) and form the supplementary stream recycled into the process and split into three supplementary sub-streams. The supplementary sub-streams are each fed proportionally via line (39) to the feed sub-stream fed via line (28) to the upper fixed-bed zone (24), the reaction mixture exiting the upper fixed-bed zone (24) via line (40), and the reaction mixture exiting the central fixed-bed zone (25) via line (41). The target temperature values for the reaction mixtures exiting the fixed-bed zones (24, 25, 26) are in each case measured by means of a temperature sensor installed beneath the fixed bed and connected to a measurement transducer (42, 43, 44), and the temperature of the feed sub-stream fed to the upper fixed-bed zone (24) and that of the reaction mixture fed to the central and lower fixed-bed zones (25, 26) are measured by means of a temperature sensor arranged above the fixed-bed zone and connected to a measurement transducer (45, 46, 47). The flow regulators (48, 49, 50) arranged in lines (39, 40, 41) for the supplementary substreams are actuated electrically via lines (51, 52, 53).

The invention claimed is:

1. Process for the preparation of $C_2$- to $C_4$-olefins from a feed stream comprising vapor-form oxygenates and steam and having a temperature of from 280 to 480° C., which is passed through at least one fixed-bed zone (3) arranged in a reactor (2) and formed from a bed of granular, shape-selective zeolite catalyst of the pentasil type, and the oxygenates are converted catalytically into olefins with high selectivity for lower olefins at a reaction temperature of from 350 to 550° C. and the reaction mixture exiting the reactor is separated into a first product stream comprising $C_2$- to $C_3$-olefins and inert gas components, at least one further, second product stream comprising $C_{4+}$-olefins, and a third product stream consisting of aqueous phase, characterized in that a reaction pressure of from 1.0 to 3.0 bara prevails at the entry of the feed stream into the fixed-bed zone (3) and a reaction pressure of from 0.5 to 2.0 bara prevails at the exit of the reaction mixture from the fixed-bed zone, and the temperature of the catalytic reaction is regulated in accordance with a target temperature value in the range from 440 to 520° C. specified for the reaction mixture exiting the fixed-bed zone by means of a supplementary stream comprising $C_{4+}$ olefins and inert gas components fed into the feed stream, wherein the target temperature value for the reaction mixture exiting the reactor is measured by means of a temperature sensor beneath the catalyst fixed bed and the temperature of the feed stream entering the reactor and flowing through the catalyst fixed bed is measured by means of a temperature sensor arranged above the catalyst mixed bed.

2. Process according to claim 1, wherein the target temperature value is in the range from 480 to 495° C.

3. Process according to claim 1 wherein, the $C_{4+}$-olefins in the second product stream together with the inert gas components and the ethylene in the first product stream are recycled into the feed stream as supplementary stream.

4. Process according to claim 1 wherein the inert gas components employed comprise steam, nitrogen, helium, neon, argon, hydrogen, carbon monoxide, carbon dioxide, $C_1$- to $C_4$-paraffins and mixtures thereof.

5. Process according to claim 1 wherein the supplementary stream comprises $C_2$- to $C_8$-olefins.

6. Process according to claim 5 wherein the supplementary stream further comprises $C_2$-olefins and $C_4$- to $C_6$-olefins.

7. Process according to claim 5 wherein the supplementary stream further comprises $C_1$- to $C_8$-paraffins.

8. Process according to claim 5 wherein the supplementary stream further comprises $C_5$- to $C_8$-naphthenes.

9. Process according to claim 5 wherein the supplementary stream further comprises $C_6$- to $C_7$ aromatic compounds.

10. Process according to claim 1 wherein by-product streams arising in thermal cracking, catalytic cracking or similar processes are employed as supplementary stream.

11. Process according to claim 1 wherein process-inherent recycling streams are employed as supplementary stream.

12. Process according to claim 1 wherein the throughput of the oxygenates present in the feed stream is from 0.1 to 10 kg, per hour and per kg of catalyst employed.

13. Process according to claim 12 wherein the throughput of the oxygenates is from about 0.3 to 1.5 kg/her per kg of catalyst used.

14. Process according to claim 1 wherein the feed stream fed to a reactor having a plurality of fixed-bed zones is split into a number of feed sub-streams corresponding to the number of fixed-bed zones, and each feed sub-stream is fed to a corresponding fixed-bed zone, the reaction mixture discharged from a fixed-bed zone is fed to the subsequent fixed-bed zone, and the reaction mixture discharged from the final fixed-bed zone in the downstream direction is fed to a separation unit, a supplementary stream comprising olefins and inert gas components is split into a number of supplementary sub-streams corresponding to the number of feed sub-streams, and each supplementary sub-stream is fed into a corresponding feed sub-stream or into the reaction mixture exiting a fixed-bed zone and fed to the subsequent fixed-bed zone.

15. Process according to claim 14 wherein the reactor has between two to six fixed bed zones.

16. Process according to claim 1 wherein the oxygenates are selected from methanol, dimethyl ether and mixtures thereof.

17. Process according to claim 1 wherein the reaction temperature is in the range of about 420° C. to about 490° C.

18. Process according to claim 1 wherein the $C_2$- to $C_4$-olefin that is produced in the process is propylene.

19. Process according to claim 1 wherein the inert gas components in the supplementary stream comprise one or more of steam, nitrogen, helium, neon, argon, hydrogen, carbon monoxide and carbon dioxide.

* * * * *